United States Patent [19]

Drivon et al.

[11] Patent Number: 5,057,633

[45] Date of Patent: Oct. 15, 1991

[54] SYNTHESIS OF PERFLUOROALKYL BROMIDES

[75] Inventors: Gilles Drivon, Saint-Martin-En-Haut; Pierre Durual, Vernaison; Elie Ghenassia, Grenoble, all of France

[73] Assignee: Societe Atochem, Puteaux, France

[21] Appl. No.: 617,128

[22] Filed: Nov. 21, 1990

[30] Foreign Application Priority Data

Nov. 24, 1989 [FR] France ................. 89 15522

[51] Int. Cl.$^5$ ................. C07C 17/22; C07C 19/08
[52] U.S. Cl. ................. 570/142; 570/137
[58] Field of Search ................. 570/142

[56] References Cited

U.S. PATENT DOCUMENTS 4,912,269 3/1990 Drivon et al. ................. 570/142

FOREIGN PATENT DOCUMENTS 298870 1/1989 European Pat. Off. ............ 570/142

Primary Examiner—J. E. Evans
Attorney, Agent, or Firm—Morgan & Finnegan

[57] ABSTRACT

The invention relates to the preparation of perfluoroalkyl bromides or bromoperfluoroalkanes $C_nF_{2n+1}$-Br (n=1 to 20).

A perfluoroalkanesulphonyl chloride $C_nF_{2n+1}$-SO$_2$Cl is reacted with a compound of formula:

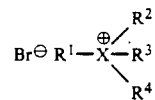

in which X represents a nitrogen or phosphorus atom and $R^1$, $R^2$, $R^3$ and $R^4$, which may be identical or different, each represent an optionally substituted hydrocarbon radical, it also being possible for one of these symbols to be a hydrogen atom.

12 Claims, No Drawings

SYNTHESIS OF PERFLUOROALKYL BROMIDES

FIELD OF THE INVENTION

The present invention relates to the field of perhalogenated aliphatic hydrocarbons and relates more particularly to the preparation of perfluoroalkyl bromides or bromoperfluoroalkanes $R_F$-Br, $R_F$ denoting a straight-chain or branched perfluoroalkyl radical $C_nF_{2n+1}$ containing from 1 to 20 carbon atoms.

BACKGROUND OF THE INVENTION

These known compounds are used in numerous fields, in particular in medicine as radiopaque agents (contrast agents to X-rays) or as oxygen transporters in blood substitutes. A compound more particularly studied in this field is n-perfluorooctyl bromide $C_8F_{17}Br$.

Among the methods disclosed for preparation of these compounds, the following may be indicated more particularly:

the action of bromine on a compound $R_F$-$SF_5$ at 500° C. in the presence of nickel (US Pat. No. 3,456,024);

the gas phase photolysis of a mixture of 1-hydrogenoperfluoroalkane and BrCl or BrF (Adcock et al., Chem. Abstr. 100 :34092e);

the action of bromine on compounds $R_F$-I in the presence of a free radical initiator such as AIBN (Japanese Application Kokai No. 85-184033);

photobromination of the same iodated compounds by UV irradiation (Huang et al., Hauxue Xuebao 1984, 42 (10) 1106-8, summarised in Chem. Abstr. 102 : 78312x).

The poor yields obtained and/or the slow kinetics of these methods are the reason that they do not permit the economic production of perfluoroalkyl bromides on an industrial scale. In view of the importance of these compounds in the medical field, it is of greatest interest to be able to produce them at the lowest possible cost.

A process for the production of perfluoroalkyl bromides from the corresponding perfluoroalkanesulphonyl chlorides $R_F$-$SO_2Cl$ has been described in Patent Application No. EP 0298870. This process, which corresponds to the following reaction scheme:

consists in reacting gaseous hydrogen bromide with a perfluoroalkanesulphonyl chloride in the presence of a catalyst consisting of an amine or a tertiary phosphine or a quaternary ammonium or phosphonium salt, at a temperature which can range from 80 to 200° C. (preferably between 90 and 150° C.); the amount of catalyst can range from 0.1 to 5 moles per 100 moles of chloride $R_F$-$SO_2Cl$ and is preferably between about 1 and 2 moles per 100. Although this process enables the perfluoroalkyl bromides to be produced in a single step, with an excellent yield and a very good selectivity, it requires the use of anhydrous gaseous HBr, a product which is expensive for a manufacturer who does not have a specific installation for the production of HBr available on his industrial site. On the other hand, in some cases, the reducing character of HBr can lead to the concomitant formation of sulphur-containing impurities (for example $R_F$-S-S-$R_F$ and $R_F$-SBr) and therefore to a drop in yield.

BACKGROUND OF THE INVENTION

It has now been found that tetrabutylammonium bromide, and more generally the compounds of formula:

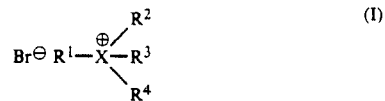

in which X represents a nitrogen or phosphorus atom and the symbols $R^1$, $R^2$, $R^3$ and $R^4$, which may be identical or different, each represent an optionally substituted hydrocarbon radical, it also being possible for one of these symbols to be a hydrogen atom, have the property of very rapidly exchanging their bromine atom for the chlorine atom of a sulphonyl chloride $R_F SO_2Cl$ and of promoting, even at low temperature, the decomposition to $R_F Br$ of the sulphonyl bromide $R_F SO_2Br$ formed as an intermediate.

Thus, provided that an at least equimolar amount of compound (I) is used, it is possible to produce the perfluoroalkyl bromides $R_F$-Br from the sulphonyl chlorides $R_F$-$SO_2Cl$ without having recourse to the use of gaseous HBr.

The invention therefore relates to a process for the preparation of perfluoroalkyl bromides, characterized in that it consists in reacting a perfluoroalkanesulphonyl chloride with an at least equimolar amount of a compound of general formula (I).

In this formula, the hydrocarbon radicals $R^1$ to $R^4$ can be, in particular, alkyl radicals containing from 1 to 16 carbon atoms and preferably 1 to 8 (for example methyl, ethyl, propyl, butyl or octyl), aryl radicals, preferably phenyl, or aralkyl radicals, preferably benzyl. These radicals, which may be identical or different, can carry one or more substituents, provided that they are not capable of reacting with the sulphonyl chloride starting material.

A particularly preferred compound of formula (I) is tetrabutylammonium bromide (designated below by the abbreviation TBAB). Other examples of compounds of formula (I) which may be mentioned, without any limitation being implied, are tetramethylammonium bromide, tetrabutylphosphonium bromide, phenyltrimethylammonium bromide, benzyltrimethylammonium bromide, tripropylamine hydrobromide and pyridine hydrobromide.

As indicated above, the compound of formula (I) must be used in an at least equimolar amount relative to the sulphonyl chloride starting material. In order to accelerate the reaction, it is generally advantageous to use the compound of formula (I) in slight excess (up to about 10%). However, it would not go beyond the scope of the present invention to use a more than 10% excess of compound (I).

The reaction according to the invention can be carried out in a concentrated medium (without solvent). It is, however, preferable to work in a solvent, chosen from the compounds which are inert towards the two reactants under the reaction conditions and have a boiling point which differs from that of the desired compound $R_F Br$. The following may be mentioned as solvents which can be used, without any limitation being implied: water, alcohols (for example methanol), halogenated aliphatic hydrocarbons, such as methylene chloride, chloroform and methylene bromide, or other solvents such as acetone, acetonitrile or toluene.

The reaction according to the invention can be carried out at a temperature ranging from ambient temperature up to about 150° C. The temperature chosen must, however, be lower than the decomposition temperature of the compound (I) used. On the other hand, in order to minimize the concomitant formation of perfluoroalkyl chloride $R_F$-Cl, it is preferable to work at below 60° C. In this respect, it is particularly advantageous to use, as solvent, methylene chloride, the boiling point of which (40° C.) enables the temperature of the reaction mixture to be controlled easily; methylene chloride is also an excellent solvent for TBAB.

A particularly preferred embodiment of the process according to the invention consists in carrying out the introduction of the compound (I) at low temperature (about 20 to 30° C.), and then keeping the reaction mixture at this temperature until the degree of conversion of the sulphonyl chloride is about 80% and finally in completing the reaction by heating to reflux.

The reaction is preferably carried out at atmospheric pressure, but it would not go beyond the scope of the present invention to work under subatmospheric or superatmospheric pressure.

The process according to the invention can be carried out equally well starting from a crude sulphonyl chloride $R_F$-SO$_2$Cl as from a sulphonyl chloride purified by distillation.

The isolation of the perfluoroalkyl bromide $R_F$-Br can be carried out in accordance with the customary techniques, for example by allowing the reaction mixture to settle, alkaline washing and fractional distillation. Yield is not substantially modified whether the sulphochloride is introduced into the compound (I) or, conversely, whether the compound (I) is introduced into the sulphochloride.

In the case where a little residual sulphonyl chloride is still present in the settled product, a small amount of fresh compound I (about 1 to 10 times the stoichiometric amount of the residual sulphonyl chloride present) may advantageously be added, before the alkaline washing step, to the settled product (preferably still hot) and the mixture allowed to settle again.

EXAMPLES

The following examples illustrate the invention without restricting it.

EXAMPLE 1

89 g of methylene chloride and 89 g (0.275 mole) of TBAB are introduced into a 500 ml glass reactor fitted with a stirrer, a dropping funnel, a condenser and a heating device, this leading to a homogeneous liquid solution at ambient temperature.

This solution is heated to 50° C. and a solution of 130 g of C$_8$F$_{17}$SO$_2$ of $\geq$99 % purity (0.250 mole) in 30 g of methylene chloride is then introduced in the course of one hour.

After the end of the addition, the reflux temperature (50-55° C.) is maintained for 3 hours.

After purging with nitrogen, the reaction mixture is allowed to settle and the following are then recovered:

an upper phase (216 g) consisting of methylene chloride, SO$_2$ (0.231 mole) and chloride (0.249 mole); and a virtually colorless lower phase (122 g), the VPC analysis of which indicates the following composition:
C$_8$F$_{17}$Br = 85.1% (which is a yield of 83%)
CH$_2$Cl$_2$ = 9.4%
C$_8$F$_{17}$SO$_2$Cl = 0.8%
C$_8$F$_{17}$Cl = 3.8%

This lower phase is then washed with 12 g of an aqueous 10% by weight sodium hydroxide solution. After allowing to settle and washing with water, a fractional distillation is carried out at atmospheric pressure. Perfluorooctyl bromide having a purity higher than 99% is thus obtained.

EXAMPLE 2

The reaction is carried out in the same equipment as in Example 1. The reactor is charged with 130 g of C$_8$F$_{17}$SO$_2$Cl and 80.5 g of TBAB. The reaction mixture is heated slowly (one hour) up to 125° C. and is then kept at this temperature for 4 hours.

By allowing to settle hot, 2 phases are covered:

an upper phase (90 g) containing 0.217 mole of Cl$\ominus$ ions; and a light yellow lower phase (115.5 g) having the following composition (VPC analysis):
C$_8$F$_{17}$Br = 89.3% (which is a yield of 82.5%)
C$_8$F$_{17}$SO$_2$Cl $\leq$ 0.1%
C$_8$F$_{17}$Cl = 9.1%

EXAMPLE 3

The reaction is carried out in the same equipment as in example 1. The reactor is charged with a solution of 80.5 g (0.25 mole) of TBAB in 87 g of methylene chloride.

A solution of 130 g of C$_8$F$_{17}$SO$_2$Cl of $\geq$99% purity (0.25 mole) in 46 g of methylene chloride is then introduced very rapidly and the reaction mixture is then kept at a temperature of between 20 and 30° C. for 24 hours, with stirring.

After the reaction mixture has settled, the following are recovered:

an upper phase (216 g) consisting predominantly of methylene chloride and containing 0.232 mole of SO$_2$ and 0.231 mole of chloride, and a virtually colorless lower phase (127 g) having the following composition:
C$_8$F$_{17}$Br = 84.3% (which is a yield of 85.5%)
CH$_2$Cl$_2$ = 99.1%
C$_8$F$_{17}$SO$_2$Cl = 4.1%
C$_8$F$_{17}$Cl = 2.3%

EXAMPLE 4

46.5 g of methylene chloride and 18.65 g (55 millimoles) of tetrabutylphosphonium bromide are charged into a 100 ml reactor equipped in the same way as in Example 1. The solution is heated to 40° C. (reflux of CH$_2$Cl$_2$) and a solution of 26 g (50 millimoles) of C$_8$F$_{17}$SO$_2$Cl in 6.5 g of methylene chloride is then introduced in the course of one hour.

The mixture is then maintained under reflux (about 42° C.) for 6 hours. After settling, the following are recovered:

an upper phase (75 g) consisting predominantly of methylene chloride and containing 45 millimoles of SO$_2$ and 45 millimoles of chloride and a virtually colorless lower phase (22 g), having the following composition:
CH$_8$F$_{17}$Br = 78.6% (which is a yield of 69%)
CH$_2$Cl$_2$ = 14.4%
C$_8$F$_{17}$SO$_2$Cl = 4.1%
C$_8$F$_{17}$Cl = 1.5%

EXAMPLE 5

A 1-liter reactor equiped as in Example 1 is charged with 652 g of a solution of $C_8F_{17}SO_2Cl$ containing 20% of $CH_2Cl_2$ (that is 1 mol of sulphochloride). Then, a solution of 355 g of TBAB (1.1 mol) in 355 g of methylene chloride is introduced within one hour at a temperature of between 20 and 30° C.

The mixture is then maintained under stirring for about 12 hours at a temperature of between 20 and 30° C., then it is brought to reflux (50±2° C.) for 12 hours.

By settling, two organic phases are separated. The lower one (477 g), consisting essentially of perfluorooctyl bromide with a little (3.9%) of residual sulphochloride, is taken up with 50 g of a 50% solution of TBAB in $CH_2Cl_2$, then heated at reflux (about 60° C.) for 2 hours.

After settling and washing with water, an organic phase (468 g) is recovered, which contains 94.8% of perfluorooctyl bromide (yield=89%) and less than 0.1% of sulphochloride. This product can be purified by distillation as in Example 1.

EXAMPLES 6 to 8

Following same operating procedure as in Example 1, the sulphochloride $C_8F_{17}SO_2Cl$ is caused to react with other bromo compounds of formula (I), namely :
Example 6 : benzyl trimethyl ammonium bromide
Example 7 : pyridine hydrobromide
Example 8 : tripropylamine hydrobromide The operating conditions and the results thus obtained are put together in the following table.

|  | EXAMPLE | | |
| --- | --- | --- | --- |
|  | 6 | 7 | 8 |
| Amounts used of: | | | |
| compound (I) | 0.22 mol | 0.31 mol | 0.32 mol |
| $C_8F_{17}SO_2Cl$ | 0.2 mol | 0.28 mol | 0.31 mol |
| $CH_2Cl_2$[a] | 190 g | 180 g | 140 g |
| Reaction time (hours)[b] | 6.75 h | 6.25 h | 7.75 h |
| Temperature | 42° C. | 42° C. | 47° C. |
| Results: | | | |
| Recovered product[c] | 108.6 g | 151.6 g | 150 g |
| Conversion rate of the sulphochloride | 93% | 71% | 100% |
| Yield in $C_8F_{17}Br$[d] | 57% | 70% | 66% |

[a]128 g per each mole of sulphochloride and the remaining for compound (I)
[b]one hour for introducing the sulphochloride solution
[c]lower phase after settling
[d]yield with respect to transformed sulphochloride

EXAMPLE 9

A solution of 89 g of TBAB in 89 g of water is charged into the same equipment as in Example 1. The solution is heated to 50° C., then 130 g of sulphocloride $C_8F_{17}SO_2Cl$ are introduced within one hour. The reaction mixture is then kept at 50° C. for 6 hours, then it is brought to reflux (101° C.) and maintained under reflux for 6 hours.

After settling, a lower phase (122 g) is recovered, which containes 48% of perfluorooctyl bromide.

EXAMPLE 10

A solution of 89 g of TBAB in 89 g of methylene chloride is charged into the same equipment as in Example 1.

Then, 105 g (0.25 mol) of $C_6F_{13}SO_2Cl$ are introduced in the course of one hour, at a temperature of between 25 and 30° C. The reaction mixture is then kept under stirring at ambient temperature for 12 hours, then under reflux (54° C.) for 12 hours.

After settling, 70 g of a product containing 89.7% of perfluorohexyl bromide are recovered.

EXAMPLE 11

One operates as in Example 10, except that $C_6F_{13}SO_2Cl$ is replaced by 80 g of $C_4F_9SO_2Cl$.

After the end of the reaction, settling allows to recover a product with a VPC purity of 96.5% ($CH_2Cl_2$ not included).

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for the preparation of perfluoroalkyl bromides, consisting of reacting a perfluoroalkanesulphonyl chloride with an at least equimolar amount of a compound of formula:

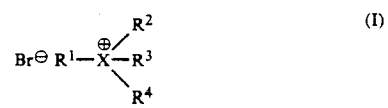

in which X represents a nitrogen or phosphorus atom and the symbols $R^1$, $R^2$, $R^3$ and $R^4$, which may be identical or different, and each represent an optionally substituted hydrocarbon radical, one of these symbols $R^1$ to $R^4$ can be a hydrogen atom.

2. Process according to claim 1, wherein the hydrocarbon radicals are optionally substituted alkyl, aryl or aralkyl radicals.

3. Process according to claim 1, wherein the compound of formula (I) is tetrabutylammonium bromide.

4. Process according to claim 1, wherein the reaction is carried out in an inert solvent having a boiling point different from the desired compound $R_FBr$.

5. Process according to claim 4, wherein the solvent is methylene chloride.

6. Process according to claim 1, wherein an excess of compound of formula (I) is used.

7. Process according to claim 1, wherein the reaction is carried out at a temperature ranging from ambient temperature up to about 150° C.

8. Process according to claim 7, wherein introduction of the compound (I) is carried out at a temperature of about 20 to 30° C., the reaction mixture is then kept at this temperature until about 80% of the sulphonyl chloride has been converted and the reaction is completed by heating to reflux.

9. Process according to claim 1, wherein perfluorooctanesulphonyl chloride is used as starting material to form perfluorooctyl bromide.

10. Process according to claim 1, wherein perfluorohexanesulphonyl chloride is used as starting material to form perfluorohexyl bromide.

11. Process according to claim 6, wherein the excess is up to about 10%.

12. Process according to claim 7, wherein the temperature is below 60° C.

* * * * *